(12) United States Patent
Aleles et al.

(10) Patent No.: US 6,818,603 B2
(45) Date of Patent: Nov. 16, 2004

(54) CLEANSING BAR CONTAINING DISCRETE ELEMENTS

(75) Inventors: Margaret Aleles, Gladstone, NJ (US); David Burwell, Princeton, NJ (US); Raymond Ip, Plainsboro, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 85 days.

(21) Appl. No.: 10/218,891

(22) Filed: Aug. 14, 2002

(65) Prior Publication Data

US 2004/0033915 A1 Feb. 19, 2004

(51) Int. Cl.⁷ .................................. A61K 7/50
(52) U.S. Cl. ................... 510/148; 510/141; 510/147; 510/151; 510/152; 510/155
(58) Field of Search ............... 510/141, 147, 510/148, 151, 152, 155

(56) References Cited

U.S. PATENT DOCUMENTS

| 4,155,870 A | 5/1979 | Jorgensen |
| 4,190,550 A | 2/1980 | Campbell |
| 4,240,760 A | 12/1980 | Levine |
| 4,335,185 A | 6/1982 | Adelman et al. |
| 4,374,175 A | 2/1983 | Tanaka |
| 4,525,411 A | 6/1985 | Schmidt |
| 5,221,506 A | 6/1993 | Dulin |
| 5,753,245 A | 5/1998 | Fowler et al. |
| 5,817,713 A | 10/1998 | Pappas et al. |
| 5,910,476 A | 6/1999 | Kinsman et al. |
| 5,937,874 A | 8/1999 | Guay et al. |
| 6,190,079 B1 | 2/2001 | Ruff |
| 6,352,948 B1 | 3/2002 | Pike et al. |
| 6,376,072 B1 | 4/2002 | Evans et al. |
| 2002/0022691 A1 | 2/2002 | Wang et al. |

FOREIGN PATENT DOCUMENTS

| GB | 1288805 A | 9/1972 |
| RU | 2086620 C | 8/1997 |

OTHER PUBLICATIONS

"Kuralon K–II" (trademark) Kuraray Co., Ltd, publiciy available prior to Aug. 14, 2002.
Package copy for "Loofah Exfoliating Soap", publicty available prior to Aug. 14, 2002.
European Search Report dated Nov. 4, 2003 for Corresponding Appln. No. EP 03 25 4942.

*Primary Examiner*—Necholus Ogden
(74) *Attorney, Agent, or Firm*—Erin M. Harriman

(57) ABSTRACT

The present invention relates to cleansing bars including: a) a cleansing composition; and b) a plurality of discrete elements having a length to diameter ratio of from about 50 to 1 to about 100,000 to 1. The cleansing bars according to the invention have good grippability, exfoliating and cleansing properties and are capable of providing a significant amount of lather in a relatively short period of time. The invention also relates to methods of making and using the cleansing bar described above.

19 Claims, 1 Drawing Sheet

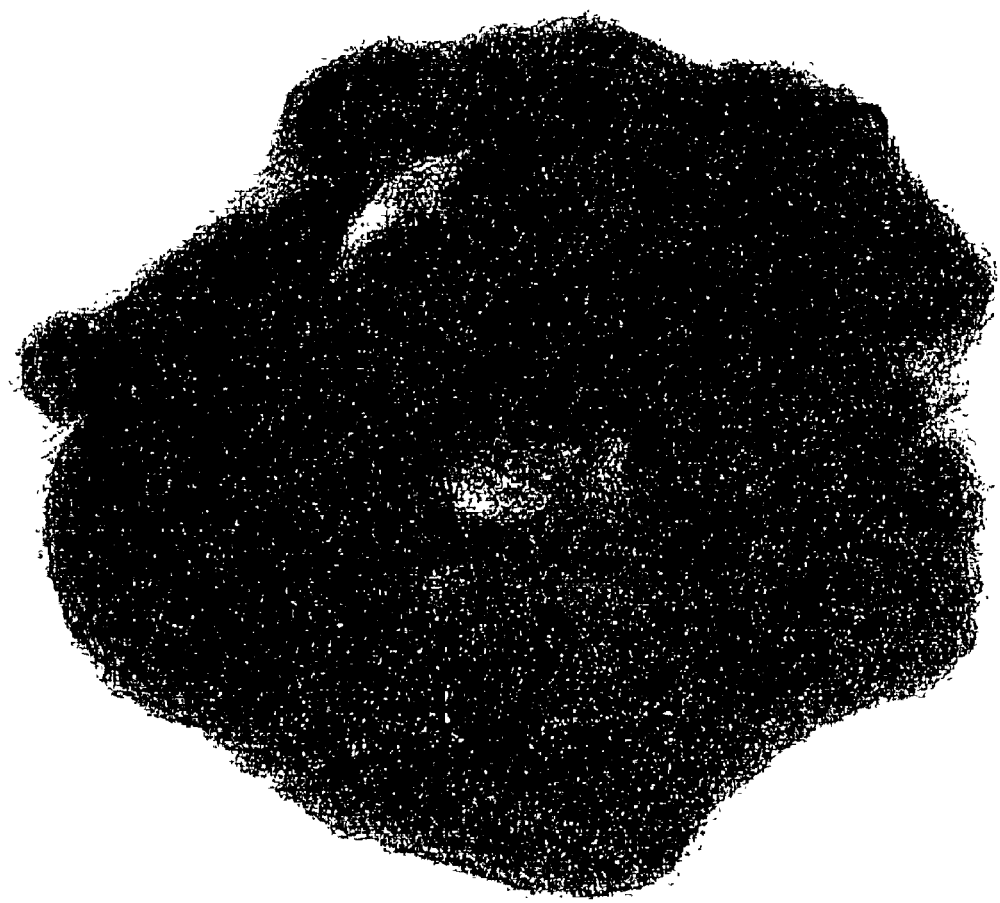

CLEANSING BAR CONTAINING DISCRETE ELEMENTS

BACKGROUND OF THE INVENTION

1. Field of the Invention

This invention relates to cleansing bars containing discrete elements. The cleansing bars have excellent lathering and cleansing properties, are useful to exfoliate skin, and have improved grippability versus conventional cleansing bars.

2. Description of the Prior Art

Conventional cleansing bars have several problems associated with them. One problem associated with cleansing bars is that they are very slippery when wet. The bars tend to slip out of the hand of the consumer during use in the shower or bath. The consumer then has to bend over or kneel down to pick up the cleansing bar from the floor of the shower.

Another problem associated with cleansing bars is that they tend not to form a lot of lather. The lather that is generated typically is slow to develop and not that abundant. Since many consumers relate lather to effectiveness of cleansing, the use of conventional cleansing bars can be viewed as providing less than optimum body cleansing.

Skin cleansing compositions having abrasive particles incorporated as scrubbing aids are known in the art. For example, LOOFAH Exfoliating Soap is a commercially available soap bar available through Earth Therapeutics. The soap bar has small particles of a chopped up loofah or puff dispersed throughout.

U.S. Pat. No. 4,155,870 discloses skin cleansing compositions comprising water-insoluble glass bubbles. Further, U.S. Pat. No. 5,910,476 discloses abrasive containing soap bars. Suitable abrasives include pumice, talc, and/or sand.

These abrasive containing cleansing compositions generally suffer from the disadvantage of having an unpleasant abrasive and/or sandy feel and may cause irritation with prolonged scrubbing.

Personal cleansing compositions containing water-insoluble micronized particles are disclosed in U.S. Pat. No. 5,753,245. The micronized particles have a defined particle size and are not tactilely perceived by the user.

U.S. Pat. No. 5,221,506 discloses a sponge core in a soap bar, i.e., a "structured soap bar." The preferred structural support is a natural synthetic open-celled sponge material.

Despite the disclosure of the prior art, there is a continuing need for a cleansing bar that has good grippability, is capable of exfoliating the skin without abrasive feel and provides a significant amount of lather in a relatively short period of time. The present invention answers this need.

SUMMARY OF THE INVENTION

It has been discovered that cleansing bar compositions having good grippability and exfoliating properties which are capable of providing a significant amount of lather in a relatively short period of time can be obtained by incorporating a plurality of discrete elements having a length to diameter ratio of from about 50 to 1 to about 100,000 to 1.Accordingly, the present invention relates to a cleansing bar comprising: a) a cleansing composition; and b) a plurality of discrete elements having a length to diameter ratio of from about 50 to 1 to about 100,000 to 1.

The invention also relates to a method for cleaning a surface comprising wetting the above described cleansing bar with water; applying agitation to the wet cleansing bar, wherein the amount of water and agitation are sufficient to create a lather on the cleansing bar, and applying said lathering cleansing bar to the surface to be cleaned.

BRIEF DESCRIPTION OF THE FIGURE

The figure is a photographic representation of the superstructure resulting the use of the cleansing bar according to Example 1.

DETAILED DESCRIPTION OF PREFERRED EMBODIMENTS

The present invention relates to a cleansing bar comprising: a cleansing composition and a plurality of discrete elements. The discrete elements have a length to diameter ratio of from about 50 to 1 to about 100,000 to 1.The cleansing bar according to the present invention may be used to treat a variety of surfaces, such as human skin or hair, animal skin or hair, clothing and fabrics, and hard surfaces, such as, for example, cars, appliances, walls, countertops, etc.

The discrete elements may be made from a wide range of materials, both natural and synthetic, so long they have a length to diameter ratio of from about 50 to 1 to about 100,000 to 1.In a preferred embodiment, the discrete elements have a length to diameter ratio of from about 100 to 1 to about 25,000 to 1, more preferably from about 500 to 1 to about 5,000 to 1.As used herein the term "diameter" means the diameter of a circular cross section of the discrete element, or in cases where the discrete element does not have a circular cross section, such as with some natural fibers or synthetic multilobal fibers, the term "diameter" means the diameter of a circle equal in area to the actual measured cross sectional area of the discrete element.

The length of the discrete element varies depending on the benefit desired. Generally, the length varies from about 0.125 to about 5.0 inches, more preferably from about 0.5 to about 3 inches and most preferred from about 1 to about 1.5 inches.

Suitable discrete elements include, but are not limited to, fibers, including but not limited to monofilament and multifilament fibers, filaments, particles, and mixtures thereof. Preferred are fibers of polyester; polyolefins, such as polyethylene and polypropylene; polyamide; rayon; cotton; hemp; wool; and combinations thereof. Examples of suitable polyamide fibers include Nylons, such as, NYLON 6, NYLON 66, and C-113 NYLON available from Dupont. Examples of polyester fibers include polyester staple fibers commercially available from KoSa, Wellman Inc., and Syntec Industries Inc.

The discrete elements useful in the present invention may be monocomponent and/or multicomponent elements of various configurations, including multi-layered structures, core-sheath structures, where the core comprises one material and the sheath comprises a different material, or multilobal structures. As is known in the art, the discrete elements may be splittable or fracturable. In another embodiment, the discrete elements may be microfibers as taught in U.S. Pat. Nos. 5,759,926 and 5,047,189, the disclosures of which are hereby incorporated by reference.

In one embodiment, the cleansing composition may be colored and the discrete elements may also colored. The discrete elements may be a color that is the same or different from the color of the cleansing composition. Alternatively, the discrete elements may be a mixture of discrete elements having different colors. Colored fibers are known in the art and may be obtained from a variety of suppliers including, for example, Martin Color-Fi, Inc. and KoSa.

In yet another embodiment, the discrete elements may be water-soluble. As used herein, "water-soluble" means that the discrete elements disperse, disintegrate, or dissolve in water. Suitable materials for water soluble discrete elements include, but are not limited to, polyethylene oxide ("PEO"), blends of PEO and polypropylene as taught in United States Patent Application 2002/022691 A1, hereby incorporated by reference. Other examples include polylactic acid fibers sold under the tradename LACTRON® by Kanebo, polysaccharides sold under the tradename LYSORB® available from Lysac Technologies Inc., and polyvinyl alcohol such as those sold under the tradename KURALON K-II available from Kuraray Co., Ltd.

In another embodiment, the discrete elements may include super absorbent polymer (SAP) fibers as described in U.S. Pat. Nos. 4,374,174; 5,817,713; 6,376,072, the disclosures of which are hereby incorporated by reference.

When the discrete element is a fiber, the denier may vary depending on the benefit desired. Typically, the denier ranges from about 0.025 to 25, more preferably from about 1.5 to about 15, and most preferred from about 3 to about 9.

The amount of the discrete elements in the cleansing bar will also vary based upon the desired benefit. Typically, the amount of discrete elements will range from about 0.01 percent to about 20 percent by weight, more preferably from about 0.1 to 10%, most preferably from about 0.5 to about 5%, based on the total weight of the cleansing bar.

One concern over the use of discrete elements in a cleansing bar is that the use of the cleansing bar frees some of the discrete elements, which may then flow to a drain in the shower, sink, or bath. The loose discrete elements may then clog the drain or be aesthetically unpleasant to the user.

Accordingly, in one embodiment of the present invention, the discrete elements have a length to diameter ratio sufficient for the elements to intertwine and/or entangle during use, thereby avoiding potential drain clogging or the unpleasant appearance of loose fibers, for example, on the surface being cleansed. In this embodiment, as the cleansing bar is used, the discrete elements become intertwined or entangled and form a superstructure. The length to diameter ratio of the discrete elements in this embodiment preferably ranges from about 100 to 1 to about 100,000 to 1, more preferably from about 100 to 1 to about 25,000 to 1, and most preferably from about 500 to 1 to about 5,000 to 1.The length of the discrete elements in this embodiment typically ranges from about 0.5 inches to about 3 inches, preferably from about 0.75 inches to about 2 inches.

The cleansing bars of the present invention include conventional cleansing compositions. Suitable cleansing compositions are solid or semi-solid at room temperature. Examples of useful cleansing compositions include, but are not limited to, fatty acid soaps, including glycerin soaps, synthetic detergents and mixtures thereof. Cleansing compositions are extensively taught in Soap Technology For the 1990's, the entirety of which is incorporated by reference.

Examples of suitable fatty acid soaps include soaps derived from hydrocarbon chain lengths of from approximately 10 to 22 (including carboxyl carbon) and may be saturated or unsaturated. The soap may be, for example, the sodium salt, potassium salt, ammonium salt, triethanolammonium salt and mixtures thereof. Examples of glycerin soaps useful in the present invention include but are not limited to those disclosed in U.S. Pat. Nos. 4,405,492 and 4,879,063, the disclosures of which are hereby incorporated by reference.

Suitable synthetic detergents include those known in the art for the desired purpose. Examples of detergents useful for personal cleansing include the isethionates, sarcosinates, and glyceryl ether sulfonates which may be pure chain length variants or those derived from commercial oils such as coconut oil.

Numerous examples of other detergents in general are included in the list appropriate for this invention. These include limited amounts of anionic acyl sarcosinates, methyl acyl taurates, N-acyl glutamates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines and mixtures thereof. Included are the alkyl ether sulfates with 1 to 12 ethoxy groups, especially ammonium and sodium lauryl ether sulfates. Alkyl chains for these other detergents are $C_8$-$C_{22}$, preferably $C_{10}$-$C_{18}$. Alkyl glucosides and methyl glucoside esters are preferred mild nonionics, which may be mixed with other mild anionic or amphoteric surfactants in the compositions of this invention.

Optional ingredients conventionally used in cleansing compositions may be incorporated into the cleansing composition of this invention. These ingredients include, but are not limited to, perfumes/fragrances, preservatives, colorants, dyes, anti-caking agents, and personal care ingredients, including, but are not limited to, skin and hair care ingredients.

Examples of suitable personal care ingredients useful in the present invention include but are not limited to safe and effective amounts of: humectants, sunscreen actives, skin soothers, anti-irritants, anti-inflammatories, emollients, conditioning agents, moisturizers, deodorants, anti-perspirants, artificial tanning agents, antimicrobial agents, anti-acne agents, anti-wrinkle agents, anti-skin atrophy agents, skin firming agents, anti-itch agents, anti-fungal agents, topical anesthetics, skin tone evening agents, active natural ingredients, agents for minimizing the appearance or retarding regrowth of unwanted hair, skin texture modifiers, and additional cleansing agents.

Emollients which can be included in the compositions of the invention function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 cetyl ether, steareth-10, oleth-8, PPG-4 lauryl ether, vitamin E acetate, PEG-7 glyceryl cocoate, lanolin, and combinations thereof. Vitamin E acetate, PEG-7 glyceryl cocoate and combinations thereof are preferred Examples of suitable humectants include polyhydric alcohols. Suitable polyhydric alcohols include, but are not limited to, glycerol (also known as glycerin), polyalkylene glycols, alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof.

Suitable skin soothers include, but are not limited to, panthenol, bisabolol, allantoin, aloe, and combinations thereof.

Suitable conditioning agents include, but are not limited to, dimethicone propyl PG-betaine, dimethicone copolyols, polyquaternium-10, guar, guar derivatives, and combinations thereof. Suitable anti-acne active ingredients include, but are not limited to, salicylic acid, sulfur, lactic acid, glycolic acid, pyruvic acid, urea, resorcinol, N-acetylcysteine, retinoic acid, benzoyl peroxide, octopirox, triclosan, azelaic acid, phenoxyethanol, phenoxypropanol, flavinoids, derivatives thereof, and combinations thereof. Salicylic acid and benzoyl peroxide are preferred.

The optional ingredients may be incorporated directly into the cleansing composition by means known in the art. Alternatively, the optional ingredients may be incorporated into or coated onto the discrete elements by means known in the art provided that the optional ingredient will sufficiently adhere to the discrete element such that it would remain in or on the discrete element until incorporated into the cleansing bar. As used herein "coated" means surface coating and/or at least partially impregnating the discrete element. The optional ingredients may be incorporated into or coated onto the discrete elements by means known in the art, for example, by treatment with an appropriate solution, suspension or slurry of the ingredient in an appropriate liquid, followed by drying by conventional means. See, for example, U.S. Pat. Nos. 4,335,185; 6,376,072; and 6,420,047, the disclosures of which are hereby incorporated by reference.

In one embodiment of the present invention, hollow fibers as taught in U.S. Pat. Nos. 3,558,420 and 5,937,874, the entirety of both are hereby incorporated by reference, are utilized to contain the optional ingredients. In this embodiment, the optional ingredients may be drawn into the fiber by capillary action or through the use of vacuum. The fibers may have walls that fracture upon use of the cleansing bar, thereby releasing the optional ingredient(s).

The cleansing bar of the present invention may be formed into a bar by any of the conventional methods known in the art, including, but not limited to, framing and the Mazzoni process. For example, the cleansing bars may be prepared by an extrusion process where chips of the cleansing composition and discrete elements are introduced into a mixer and mechanical agitation is applied to evenly distribute the discrete elements among the cleansing composition chips. The chip-discrete element mixture is then transferred into a plodder for extrusion into a long cleansing bar. The long bar can then be cut into the desirable sizes/shapes.

In another embodiment, the cleansing bars may be prepared by heating the cleansing composition to a temperature above its melting point (typically about 70° C. to about 130° C.). The discrete elements are then added to the melted composition and mixed. The mixture is then typically cooled. Optional ingredients like perfume, skin care ingredients, and colorants are typically added when the temperature reaches below about 90° C. The molten stock is then poured into suitable molds of different forms made of plastic or rubber and allowed to cool and harden at ambient conditions.

If desirable, the cleansing bar compositions may be aerated such that the bar will float in water.

As discussed above, it has been discovered that cleansing bar compositions having good grippability and exfoliating properties which are capable of providing a significant amount of lather in a relatively short period of time can be obtained by incorporating a plurality of discrete elements having a length to diameter ratio of from about 50 to 1 to about 100,000 to 1. Additionally, it has been discovered that a substantially smaller amount of the cleansing bar according to the invention is needed to achieve an equivalent level of cleansing when compared to conventional cleansing bars. Accordingly, because a smaller amount of cleansing composition comes into contact with the surface being cleaned, less unnecessary surface damage or irritation is expected.

EXAMPLES

The following examples will more fully illustrate the embodiments of this invention. All parts, percentages and proportions referred to herein are by weight unless otherwise indicated. The examples are provided for illustrative purposes and should not be construed as limiting the scope of the invention.

Example 1

Cleansing Bar Containing Polyester Fiber

A cleansing bar was prepared using a clear glycerin soap base (available as "Moisturizing Clear Glycerin Soap" by Life of the Party™, available in the form of a 2-lb soap brick). Small cubes were cut from the soap brick and placed into a graduated glass container. The soap cubes were then melted using a microwave oven. 0.6 grams of solution dyed purple polyester fibers available from Martin Color-Fi, Inc. (6 denier, 2" long, length to diameter ratio=2042) were then placed into a soap mold before 80 grams of the molten soap was poured in. After the mixture cooled down, the cleansing bar was removed from the mold.

The cleansing bar was used as a conventional soap bar until the cleansing composition was used up. As the cleansing bar was used, the discrete elements (polyester fibers) began to entangle and form a superstructure. The figure is a photographic representation of the superstructure remaining after the cleansing composition was used up.

Example 2

Cleansing Bar Containing Wool Fibers

A cleansing bar was prepared using a clear glycerin soap base (available as "Moisturizing Clear Glycerin Soap" by Life of the Party™, available in the form of a 2-lb soap brick). Small cubes were cut from the soap brick and placed into a graduated glass container. The soap cubes were then melted using a microwave oven. Merino wool fibers available from Gavanbay Fibers (4.12 denier) were first cut to a length of 1.5" (giving a length to diameter ratio=1814); then, 0.6 grams of such fibers were placed into a soap mold before 80 grams of the molten soap was poured in. After the mixture cooled down, the cleansing bar was removed from the mold.

Example 3

Cleansing Bar Containing Nylon Fibers

A. General Procedure

Cleansing bars were prepared using a white glycerin soap base (available as "Moisturizing White Glycerin Soap" by Life of the Party™, available in the form of a 2-lb soap brick). To prepare a cleansing bar, small cubes were cut from the soap brick and placed into a graduated glass container. The soap cubes were then melted using a microwave oven. The molten soap could then be poured into different shapes and sizes of cleansing bar molds, cooled, then removed from the molds. Cleansing bars containing nylon fibers were prepared in a similar fashion except that a specific amount of nylon fibers were placed into soap molds before the molten soap was poured in. The nylon fibers were stirred in the molten soap, then the mixtures were cooled and the cleansing bars were removed from the molds.

Cleansing bars were prepared in pairs (one with nylon fibers and one without). The two bars in each pair were matched in shape and size and were of equivalent weight.

Pairs of varying shapes and sizes (approximately 60 grams) were prepared. For each cleansing bar containing nylon fibers, 0.7 grams of DuPont C-113 Nylon fibers (6 denier, 1.5" long) was added.

B. Richer Lather Production

Two cleansing bars of equivalent weight (approximately 60 grams) were prepared as described above. The bars were the same except 0.7 grams of DuPont C-113 Nylon fibers (6.0 denier, 1.5" long, length to diameter ratio=1,463) was added to one of the bars while the other bar contained no discrete elements.

Ten panelists were recruited for this study. First, one of the two cleansing bars was wetted under water and rubbed 10 times on the hand of each panelist in a circular motion. The panelists were then asked to note the amount of lather generated by this bar. Afterwards, the lather was scraped off from the hands with a tongue depressor and placed on a tared weighing dish. The weight of the lather was measured and recorded. The same procedure was repeated using the other cleansing bar. The panelist was asked to pick which of the cleansing bars produced a richer lather. The weight of the lather generated by the two cleansing bars was also compared.

Results

As seen in Table 1 below, for nine out of ten panelists, the weight measurements indicated that the cleansing bar containing discrete elements generated more lather than the plain cleansing bar. On average, the cleansing bar of the invention produced 0.2248 grams of lather versus 0.1430 grams by the conventional bar. This difference is statistically significant based on a paired t-test (p<0.002). Nine panelists also reported that the cleansing bar of the invention produced a richer lather than the conventional bar.

TABLE 1

| Panelist Number | Lather Production (grams) | | User Opinion |
| --- | --- | --- | --- |
| | Discrete Elements | Plain Soap | Which gives richer foam/lather? |
| 1 | 0.2381 | 0.1556 | Discrete Elements |
| 2 | 0.2212 | 0.1113 | Discrete Elements |
| 3 | 0.1625 | 0.0453 | Discrete Elements |
| 4 | 0.1827 | 0.1281 | Discrete Elements |
| 5 | 0.0995 | 0.1734 | Discrete Elements |
| 6 | 0.3344 | 0.2390 | Discrete Elements |
| 7 | 0.2243 | 0.1136 | Discrete Elements |
| 8 | 0.2703 | 0.1963 | Plain Soap |
| 9 | 0.2468 | 0.1124 | Discrete Elements |
| 10 | 0.2683 | 0.1548 | Discrete Elements |
| Average | 0.2248 | 0.1430 | |

Conclusion

The data from this study indicated that a cleansing bar having a plurality of discrete elements was able to generate a richer lather than a plain cleansing bar.

C. Quick Lather Production

Two cleansing bars of equivalent weight (approximately 60 grams) were prepared using two identical soap molds as described above in A. The cleansing bars were the same except 0.7 grams of DuPont C-113 Nylon fibers (6.0 denier, 1.5" long, length to diameter ratio=1,463) was added to one of the bars while the other bar contained no discrete elements.

Seven panelist were recruited for this study. First, panelists were asked to wash their hands with one of the two cleansing bars (rubbed the bar in circular motions on the hands) for a fixed time period of 5 seconds. Afterwards, the lather was scraped off from the hands with a tongue depressor and placed on a tared weighing dish. The weight of the lather was measured and recorded. The same procedure was repeated using the other cleansing bar. The weight of the lather generated by the two cleansing bars was compared.

Results

As seen in Table 3 below, for six out of seven panelists, the weight measurements indicated that the cleansing bar of the invention generated lather faster than the plain cleansing bar. On average, the cleansing bar having a plurality of discrete elements produced 0.2290 grams of lather versus 0.1357 grams by the plain cleansing bar after 5 seconds of rubbing. This difference is statistically significant based on a paired t-test (p <0.025).

TABLE 3

| Panelist Number | Lather Production (grams) | |
| --- | --- | --- |
| | Invention | Plain |
| 1 | 0.4430 | 0.2410 |
| 2 | 0.1581 | 0.1039 |
| 3 | 0.1207 | 0.1512 |
| 4 | 0.1628 | 0.0939 |
| 5 | 0.2256 | 0.1622 |
| 6 | 0.2574 | 0.0646 |
| 7 | 0.2356 | 0.1328 |
| Average | 0.2290 | 0.1357 |

Conclusion

The data from this study indicated that a cleansing bar having a plurality of discrete elements was able to generate lather faster than a plain cleansing bar.

D. Superior Cleansing/Exfoliation

Two cleansing bars of equivalent weight (approximately 60 grams) were prepared using two identical soap molds as described above in A. The cleansing bars were the same except 0.7 grams of DuPont C-113 Nylon fibers (6.0 denier, 1.5" long, length to diameter ratio=1,463) were added to one of the bars while the other bar contained no discrete elements. A cube of 0.75"×0.75"×0.75" was cut out from each of these cleansing bars for the following testing.

Ten squares of 2"×2" were cut out from a transparency film. In the center of each square, a test site of 0.5"×0.5" was marked using a permanent marker. The weight of all 10 transparency squares was measured and recorded. Approximately 0.01 grams of mascara was applied to and spread across evenly on each test site. The mascara was allowed to air-dry. Upon drying, five of the squares were cleansed using the cleansing cube of the invention (the cube was stroked in a back-and-forth motion across the test site 10 times). The other five squares were cleansed using the plain cleansing cube. After cleansing, all 10 squares were rinsed under tap water to wash off the residual cleanser. After gentle blot-drying, each square (along with the left-behind mascara) was re-weighed. The amount of mascara removed was then calculated for the two groups (the group cleansed with the cleansing bar of the invention and the group cleansed with the plain cleansing bar).

Results

As seen in Tables 5 and 6 below, the cleansing bar having a plurality of discrete elements provided a more superior cleansing and exfoliation than the plain cleansing bar. On average, 0.0068 grams of mascara were removed by the cleansing bar of the invention, while only 0.0020 grams were removed by the plain cleansing bar. A t-test revealed that the difference in cleansing and exfoliating abilities between the two bars was statistically significant (p <0.0001).

TABLE 5

Data for Cleansing Bar Having Discrete Elements

| | Weight of Transparency + Mascara (grams) | | | | |
|---|---|---|---|---|---|
| Test | Before | After | | Weight of Mascara | |
| Site Number | Mascara Application | Mascara Application | After Soap Cleansing | Amount Applied | Amount Removed |
| L1 | 0.3306 | 0.3405 | 0.3321 | 0.0099 | 0.0084 |
| L3 | 0.3337 | 0.3437 | 0.3374 | 0.0100 | 0.0063 |
| L5 | 0.3229 | 0.3328 | 0.3264 | 0.0099 | 0.0064 |
| L7 | 0.3561 | 0.3661 | 0.3597 | 0.0100 | 0.0064 |
| L9 | 0.3359 | 0.3458 | 0.3392 | 0.0099 | 0.0066 |
| | | | Average | 0.0099 | 0.0068 |

TABLE 6

Data for Conventional Cleansing Bar

| | Weight of Transparency + Mascara (grams) | | | | |
|---|---|---|---|---|---|
| Test | Before | After | | Weight of Mascara | |
| Site Number | Mascara Application | Mascara Application | After Soap Cleansing | Amount Applied | Amount Removed |
| L2 | 0.3456 | 0.3557 | 0.3534 | 0.0101 | 0.0023 |
| L4 | 0.3556 | 0.3658 | 0.3638 | 0.0102 | 0.0020 |
| L6 | 0.3439 | 0.3537 | 0.3518 | 0.0098 | 0.0019 |
| L8 | 0.3570 | 0.3669 | 0.3656 | 0.0099 | 0.0013 |
| L10 | 0.3586 | 0.3684 | 0.3660 | 0.0098 | 0.0024 |
| | | | Average | 0.0100 | 0.0020 |

Conclusion

The data from this study indicated that a cleansing bar according to the invention provided cleansing and exfoliation that were superior to a conventional cleansing bar.

E. Less Irritation

Two cleansing bars of equivalent weight (approximately 60 grams) were prepared using two identical soap molds. The bars were the same except 0.7 grams of DuPont C-113 Nylon fibers (6.0 denier, 1.5" long, length to diameter ratio=1,463) was added to one of the bars while the other bar contained no discrete elements. A cube of 0.75"×0.75"×0.75" was cut out from each of these cleansing bars for the following testing.

Conventional soaps contain surfactants that are known to damage the skin and induce signs of irritation like erythema and dryness. Therefore, the smaller the amount of soap used, the less the amount of irritation should be.

Ten squares of 2"×2" were cut out from a transparency film. In the center of each square, a test site of 0.5"×0.5" was marked using a permanent marker. The weight of all 10 transparency squares was measured and recorded. Then, 0.004 grams of light brown foundation makeup was applied to and spread across evenly on each test site. The foundation was allowed to air-dry. Upon drying, five of the squares were cleansed using the cleansing cube having discrete elements—the cube was stroked across the test site (each stroke dispenses about 0.002 grams of soap on average). The number of strokes needed to completely clean off the foundation was recorded for each of 5 squares. The same procedure was followed for the other 5 squares except the plain cleansing bar was used instead.

Results

As seen in Table 7 below, relative to the plain cleansing bar, a substantially fewer number of strokes was needed to achieve an equivalent level of cleansing when a cleansing bar having discrete elements according to the invention was used. On average, it took 1.6 strokes of the cleansing bar of the invention to clean the foundation, whereas 23.6 strokes of the ordinary cleansing bar was needed. This difference, as demonstrated by a t-test, was statistically significant ($p<0.0001$).

TABLE 7

Number of Strokes needed to achieve a similar level of cleansing

| Invention | | Ordinary Bar | |
|---|---|---|---|
| Test Site | # Strokes | Test Site | # Strokes |
| 1A | 2 | 1B | 20 |
| 2A | 1 | 2B | 25 |
| 3A | 2 | 3B | 23 |
| 4A | 2 | 4B | 25 |
| 5A | 1 | 5B | 25 |
| Average | 1.6 | Average | 23.6 |

Conclusion

This study demonstrated that a substantially fewer number of strokes was needed to achieve an equivalent level of cleansing when a cleansing bar containing discrete elements according to the invention was used. Therefore, the skin would be less exposed to damaging surfactants, and thus less likely to suffer from irritation.

F. Soap Grippability

Six cleansing bars were prepared from identical molds, having equivalent size, shape, and weight as described in A above. Added to three of the bars was 0.7 grams of DuPont C-113 Nylon fibers (6.0 denier, 1.5" long, length to diameter ratio=1,463) (referred to as discrete element bars 1–3) whereas no discrete elements were added to the other three bars (referred to as plain bars 1–3 below).

A "grippable" soap bar does not slip easily. Therefore, a grippable bar should be more resistant to slipping/sliding down a slanted surface than one that is more slippery (not as grippable).

A 14-degree slanted surface was created using a lab jack and a flat board. A transparency film was placed on the board to provide a completely smooth surface. A starting line and a finish line (5.5" apart) were marked on the board. A discrete element bar and a plain bar were wetted thoroughly by hand through circular rubbing motions. The two bars were placed side by side at the starting line. The bars were then released. The process was repeated for discrete element bar 2 and plain bar 2 and discrete element bar 3 and plain bar 3. The time it took each bar to reach the finish line was recorded.

Results

As seen in Table 8 below, the plain cleansing bars always reached the finish line before the cleansing bar of the invention. On average, the plain bars slipped down the slanted board in half the time it took the cleansing bars having discrete elements (3.0 seconds versus 6.3 seconds). The difference was statistically significant ($p<0.04$). In other words, the plain cleansing bars tended to be more slippery than those made according to the invention.

TABLE 8

Time for the Cleansing Bar to Reach The Finish Line

| Discrete Elements | | Plain Bar | |
| --- | --- | --- | --- |
| Bar | Time (sec) | Bar | Time (sec) |
| 1 | 11 | 1 | 7 |
| 2 | 3 | 2 | 1 |
| 3 | 5 | 3 | 1 |
| Average | 6.3 | Average | 3.0 |

Conclusion

The data from this study indicated that the cleansing bars of the invention were easier to grip and less likely to slip than plain cleansing bars.

Example 4

Comparative Example

Two cleansing bars of equivalent weight (approximately 60 grams) were prepared using 2 identical soap molds as described in Example 3A above. The bars were the same except 0.7 grams of Induchem INDUCOS 13/4 polyethylene beads with a length to diameter ratio of less than 10 was added to one of the bars while the other bar contained no discrete elements.

Ten panelists were recruited for this study. First, one of the two cleansing bars was wetted under water and rubbed 10 times on the hand of each panelist in a circular motion. Afterwards, the lather was scraped off from the hands with a tongue depressor and placed on a pre-weighed dish. The combined weight of the dish and the lather was measured and recorded. The weight of lather produced was then calculated by subtracting the weight of the dish from the combined weight of the dish and lather. The same procedure was repeated using the other cleansing bar. The weight of the lather generated by the two cleansing bars was also compared.

Results

As seen in Table 2 below, for half of the panelists, the cleansing bar containing polyethylene beads generated more lather than the plain cleansing bar. For the other half of the panelists, however, the plain bar generated more lather than the bar with beads. On average, the cleansing bar with beads produced 0.1594 grams of lather while the conventional bar produced 0.1563 grams. The difference between the two bars is not statistically significant based on a paired t-test (p=0.890).

TABLE 2

| Panelist Number | Weight (grams) | | | | | |
| --- | --- | --- | --- | --- | --- | --- |
| | Dish Alone | | Dish + Lather | | Lather Produced | |
| | Plain | Beads | Plain | Beads | Plain | Beads |
| 1 | 6.0293 | 5.9203 | 6.1903 | 6.0343 | 0.1610 | 0.1140 |
| 2 | 6.0526 | 5.9542 | 6.2892 | 6.1072 | 0.2366 | 0.1530 |
| 3 | 6.0436 | 5.9263 | 6.2299 | 6.0426 | 0.1863 | 0.1163 |
| 4 | 6.0446 | 6.0212 | 6.2506 | 6.2510 | 0.2060 | 0.2298 |
| 5 | 5.9859 | 5.9809 | 6.1121 | 6.1142 | 0.1262 | 0.1333 |
| 6 | 5.9488 | 5.9736 | 6.1503 | 6.2395 | 0.2015 | 0.2659 |
| 7 | 6.0158 | 6.0053 | 6.0636 | 6.1530 | 0.0478 | 0.1477 |
| 8 | 6.0020 | 5.9453 | 6.2686 | 6.1667 | 0.2666 | 0.2214 |

TABLE 2-continued

| Panelist Number | Weight (grams) | | | | | |
| --- | --- | --- | --- | --- | --- | --- |
| | Dish Alone | | Dish + Lather | | Lather Produced | |
| | Plain | Beads | Plain | Beads | Plain | Beads |
| 9 | 5.9266 | 5.9884 | 6.0235 | 6.0508 | 0.0969 | 0.0624 |
| 10 | 5.9541 | 6.0281 | 5.9885 | 6.1783 | 0.0344 | 0.1502 |
| | | | | AVERAGE | 0.1563 | 0.1594 |

Conclusion

The data from this study indicated that a cleansing bar having polyethylene beads (having a length to diameter ratio outside of the length to diameter ratio of the cleansing bars of the claimed invention) did not consistently generate a richer lather than a plain cleansing bar. In contrast, as shown by Examples 3B and 3C above, cleansing bars according to the invention, containing discrete elements having a length to diameter ratio of from about 50 to 1 to about 100,000 to 1 consistently generated a lather that was richer than that generated by plain cleansing bars.

What is claimed:

1. A cleansing bar comprising:
   a) a cleansing composition; and
   b) a plurality of discrete elements having a length to diameter ratio of from about 50 to 1 to about 100,000 to 1, wherein the discrete elements have a length ranging from about 0.125 to about 5.0 inches.

2. The cleansing bar according to claim 1, wherein the cleansing composition comprises fatty acid soaps, synthetic detergents, and mixtures thereof.

3. The cleansing bar according to claim 1, wherein the discrete elements have a length to diameter rate of from about 100 to 1 to about 25, to 1.

4. The cleansing bar according to claim 3, wherein the discrete elements have a length to diameter ratio of from about 500 to 1 to about 5,000 to 1.

5. The cleansing bar according to claim 1, wherein the length of the discrete elements range from about 0.5 to about 3.0.

6. The cleansing bar according to claim 1, wherein the discrete elements intertwine and/or entangle during use.

7. The cleansing bar according to claim 6, wherein the length to diameter ratio is from about 100 to 1 to about 100,000 to 1.

8. The cleansing bar according to claim 1, wherein the amount of discrete elements ranges from about 0.01 percent to about 20 percent by weight, based on the total weight of the cleansing bar.

9. The cleansing bar according to claim 8, wherein the amount of discrete elements ranges from about 0.5 to about 5.0 percent by weight, based on the total weight of the cleansing bar.

10. The cleansing bar according to claim 1, wherein the discrete elements are fibers having a denier of from about 0.025 to about 25.

11. The cleansing bar according to claim 10, wherein the fibers have a denier of from about 3 to about 9.

12. The cleansing bar according to claim 10, wherein the fibers are selected from polyester, polyolefin, polyamide, rayon, cotton, hemp, wool, and combinations thereof.

13. The cleansing bar according to claim 12, wherein the fibers are selected from nylon fibers, polyester fibers, and mixtures thereof.

14. The cleansing bar according to claim 1, wherein the discrete elements are water-soluble.

15. The cleansing bar according to claim 14, wherein the discrete elements are selected from polyethylene oxide fibers, polyethylene oxide-propylene blend fibers, polylactic acid fibers, polysaccharides fibers, polyvinyl alcohol fibers, and mixtures thereof.

16. The cleansing bar according to claim 1, wherein the discrete elements are superabsorbant polymers.

17. The cleansing bar according to claim 1, further comprising a personal care ingredient.

18. The cleansing bar according to claim 17, wherein said personal care ingredient is incorporated into the discrete elements, coated onto the discrete elements, or is a mixture thereof.

19. The cleansing bar according to claim 17, wherein file personal care ingredient is selected from tile group consisting or a skin care ingredient, a hair care ingredient, a deodorant, an anti-perspirant, and mixtures thereof.

* * * * *